United States Patent

Plant Pat. 3,689

Patented Mar. 11, 1975

3,689

**BROMELIACEAE PLANT—*CRYPTANTHUS BIVITTATUS MINOR* (cv) PINK STARLIGHT**

Barnell L. Cobia, Winter Garden, Fla., assignor to B. L. Cobia, Inc., Winter Garden, Fla.

Filed Jan. 28, 1974, Ser. No. 437,317

**Int. Cl. A01h *5/12***

U.S. Cl. Plt.—88 1 Claim

ABSTRACT OF THE DISCLOSURE

A new and distinct plant variey of the Bromeliaceae family has elongated leaves which have prominent albino marginal areas that in color are dominated by red, pink and/or yellowish pink hues when subjected to prolonged light exposure and which have an intervening prominent chlorophyllous center area that generally extends along and laterally of the leaf axis. The center area has striations which in varying degrees exhibit albino characteristics and the inflorescence has fewer and light colored flowers with fewer ovules than specimens of the *Cryptanthus bivittatus minor* variety.

The invention relates to a new and distinct plant variety of the Bromeliaceae family and which has been named the *Cryptanthus Bivittatus minor* (cv) Pink Starlight by the inventor.

Certain plants of the Bromeliaceae family are known in the foliage plant market and among these are those of the *Cryptanthus bivittatus minor* variety. Specimens of this variety have leaves that are characterized by prominent chlorophyllous marginal areas and a prominent chlorophyllous center area that extends along the leaf axis and is separated from the chlorophyllous marginal areas by intervening albino areas that are usually laterally offset from the axis of the leaf. The hypodermis at the upper epidermal side of the leaves contain anthocyanin which imparts a reddish cast to the leaves. In the chlorophyllous areas the cast tends to mask the green coloring of the chlorophyl and to produce a brownish appearance. The reddish cast is most pronounced in those leaves which have been subjected to the most intense light exposure and the cast tends to diminish somewhat in those leaves which are shaded in the growing environment. The intensity also varies seasonally in accord with day lengths and other light controlling conditions.

Another variety of the Bromeliaceae family found in the marketplace is the *Cryptanthus bivittatus minor* (cv) Starlight variety. This variety was developed by the inventor from a mutation that appeared on a plant specimen of the *minor* variety. The chief characteristic that distinguishes this variety from the *minor* variety is the notable absence of the chlorophyllous areas along the axis of the leaves. The leaves accordingly have chlorophyllous marginal areas that are separated by a fairly well defined intervening albino area that spans the length of the leaf along the laterally of the leaf axis. Little change has been detected in the anthocyanisn pigmentation and hence the chlorophyllous marginal leaf areas have a brownish appearance and the albino leaf area has a reddish cast, all of which varies with the light exposure and seasonal growing conditions in the manner of such changes in specimens of the *minor* variety.

Experience has shown that specimens of the Starlight variety are more appealing to the purchasing public than those of the *minor* variety. This is attributed to the fact that the Starlight variety has a larger and more prominent albino area in which the reddish cast of the anthocyanin pigmentation can be noted by the purchaser.

A general object of the invention has been to develop a variety of the Bromeliaceae family which can be distinguished from the *minor* and Starlight varieties of this family and which also has substantial albino areas in the leaves in which the appealing reddish cast can be detected by purchasers. The objects of the invention have been fully realized by the development of the new plant variety hereinafter described in detail.

The new variety was developed in a nursery located at Winter Garden, Fla., and appeared as a mutation on a plant specimen of the *Cryptanthus bivittatus minor* variety which was then under cultivation at the nursery. Since the initial discovery of the new variety, the plant variety has been asexually reproduced by the inventor at the Winter Garden nursery through the propagation of vegetative offshoots taken from the original plant exhibiting the muted characteristics.

Through successive propagations, it has been ascertained that plant specimens of the new variety generally resemble specimens of both of the aforementioned varieties in physical size but are nevertheless distinguishable therefrom and from specimens of other related varieties known to the inventor by a growth habit which is evident in plants propagated and grown under nursery conditions utilized in the growing of tropical plants at Winter Garden, Fla., as embodying the following principal characteristics:

1. Elongated leaves which have prominent albino marginal areas that are separated in the leaf structure by an intervening prominent chlorophyllous center area that generally extends along the leaf axis, which contain striations in the chlorophyllous center area that exhibit albino characteristics, and which develop, upon prolonged exposure to sunlight, colors in the albino marginal areas that are dominated by red, pink and/or yellowish pink hues, and 2. An inflorescence which in comparison to that of the *minor* variety has fewer and lighter colored flowers that have fewer ovules.

The accompanying drawings serve, by color photographic means, to illustrate the new plant variety and wherein.

Figure 1:
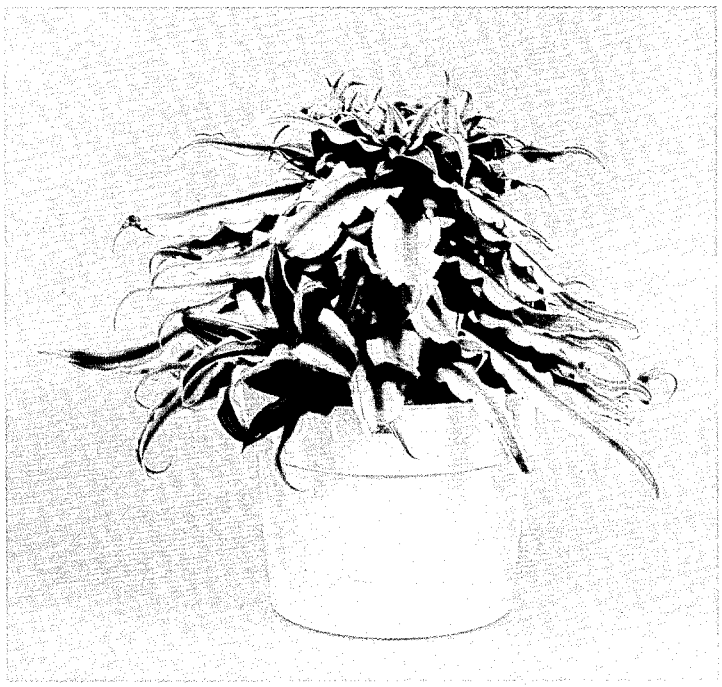
FIG. 1 is a color photograph of a plant specimen of the new plant variety as seen approximately five weeks after anthesis.
Figure 2:
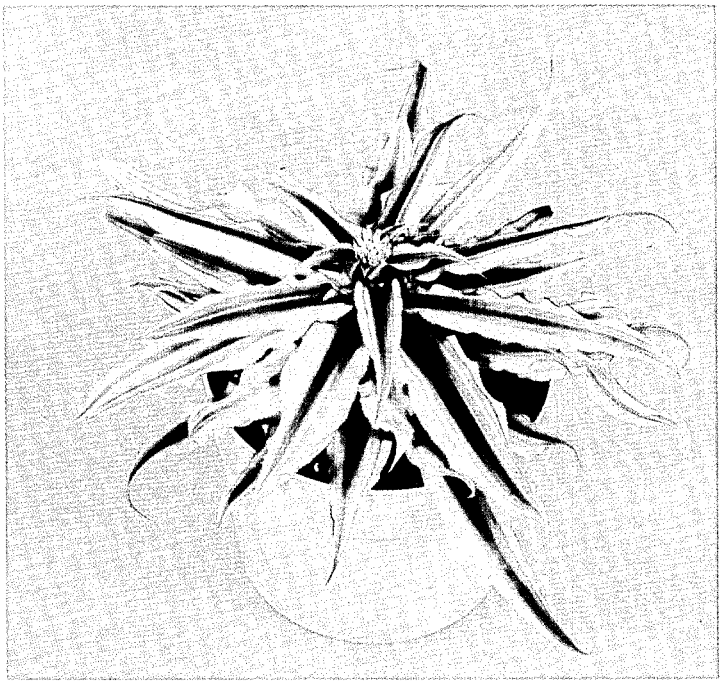
FIG. 2 is a color photograph showing yet another specimen of the new plant variety as seen in full bloom.
Figure 3:
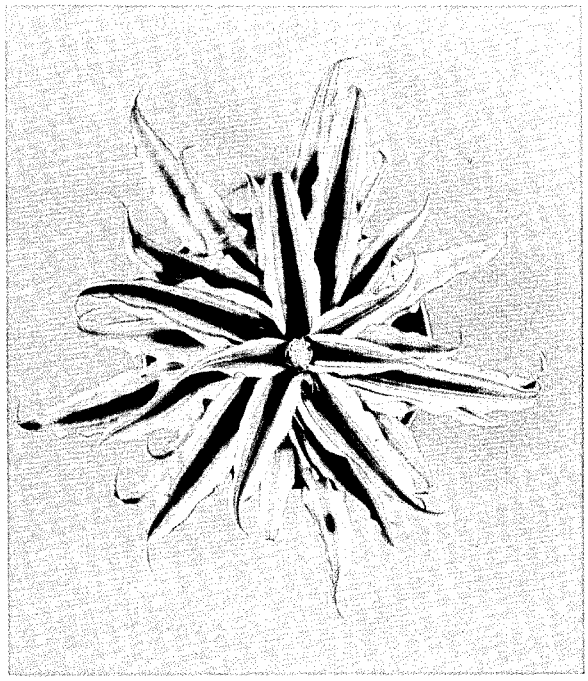
FIG. 3 is another color photograph of a specimen of the new plant variety as seen at the beginning of anthesis.
Figure 4:
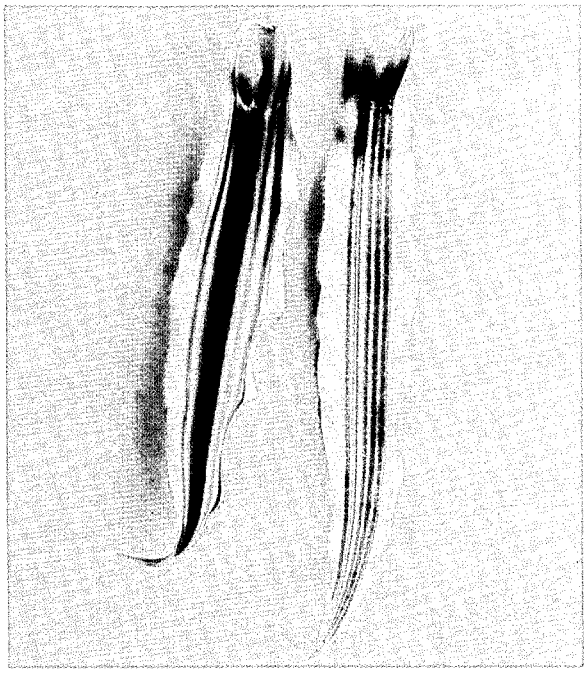
FIG. 4 is a color photograph showing the upper and lower surfaces of two leaves taken from a specimen of the new plant variety.

The following is a detailed description of the new plant variety with colors and hues, unless otherwise clearly indicated by the text through the absence of color notations, being named in accord with the ISCC-NBS Method of Designating Colors (U.S. Dept. of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plant specimens which generally range in age from seven to ten months from initial propagation, and which were grown under 50–70% shaded glasshouse nursery conditions in the Winter Garden, Florida area where temperatures generally range from 60–85° F. during the winter months, from 75–95° F. during the summer months and are ambient during intervening periods.

DETAILED PLANT DESCRIPTION

Name: *Cryptanthus bivittatus minor* (cv) Pink Starlight.

Origin: A vegetative mutation on a plant of the *Cryptanthus bivittatus minor* variety.

Classification:

*A. Botanic.*—Bromeliaceae or pineapple family.
*B. Commercial.*—Foliage plant.

Form: Terrestrial, depressed herb having densely rosulate spreading leaves and bearing rootable offshoots that initiate during or subsequent to anthesis, and with growth terminating with anthesis.

Stems:

*A. General.*—Short, upright and sheathed by overlapping leaves and having a latent bud in the axil areas.
*B. Texture.*—Glabrous and fleshy.
*C. Size.*—1. Length—Usually between 30 and 80 mm. at anthesis. 2. Diameter—Usually between 4 and 15 mm. anthesis.
*A. General.*—Simple and sessile with stem sheathing leaf bases.
*B. Texture.* — 1. Upper epidermal area—Glabrous and relatively smooth. 2. Lower epidermal area—Punctate with densely appressed white lepidote and peltate hairs.
*C. Arrangement.*—Rosulate.
*D. Margins.*—Undulating and finely toothed with distally recurving small spines.
*E. Venation.*—Parallel and obscure.
*F. Shape.*—Lanceolate to linear with long acuminate recurved tip, and commonly irregularly spiraled.
*G. Size (at anthesis).*—1. Length—Usually between 50 and 170 mm. below the apex and with diminishing length dimensions in the apex area. 2. Width—Usually between 15 and 31 mm. at the widest area distally of the stem sheathing basal area. 3. Thickness—Usually between 1 and 3.5 mm. along the axis and thinning laterally thereof to between .2 and 0.9 mm. at the margins and with some evidence of a general taper along the leaf axis toward the tip.
*H. Color.*—1. General—Prominent albino marginal areas which upon prolonged exposure to light are in color dominated by red, pink and/or yellowish pink hues, and which are separated by an intervening prominent chlorophyllous area that generally extends along and laterally of the leaf axis and has striations which in varying degrees exhibit albino characteristics. 2. Albino marginal areas—Commonly moderate red (2.5 R 5/10) (near 2.5 R 4/10) (5 R 5/10) (5 R 4/10), deep pink (near 10 RP 6/10) (near 10 RP 6/8) (2.5 R 6/10) (2.5 R 6/8) (5 R 6/10) (5 R 6/8), strong pink (10 RP 7/8) (2.5 R 7/8), moderate pink (near 2.5 R 7/4) (5 R 7/6) (near 5 R 7/4), strong yellowish pink (5 R 7/8), and/or moderate yellowish pink (near 7.5 R 7/4) when subjected to prolonged exposure (two weeks) to sunlight during the summer months. 3. Chlorophyllous area—Commonly dark greyish red-blackish red-very dark red (near 2.5 R 2/2) (5 R 2/2), dark greyish red (2.5 R 3/2) (5 R 3/2), dark greyish reddish brown (near 7.5 R 2/2) (10 R 2/2), and greyish reddish brown (7.5 R 3/2) (10 R 3/2) in most densely chlorophyllous areas when subjected to prolonged exposure (two weeks) to sunlight during summer months and commonly light greyish reddish brown (near 5 YR 6/2), light greyish brown (5 YR 6/2) (7.5 YR 6/2), light greyish yellowish brown (10 YR 6/2), light olive brown (2.5 YR 6/2) (near 2.5 YR 5/4), light brown (5 YR 5/4) (7.5 YR 5/4), moderate yellowish brown (10 YR 5/4), moderate yellowish pink (2.5 YR 7/4) (5 YR 7/4), and/or moderate yellowish pink-moderate orange (near 2.5 YR 7/6) in chlorophyl containing striations exhibiting albino characteristics when subjected to prolonged exposure (two weeks) to sunlight during the summer months, and with colors common to the albino marginal areas in the striation in the center area that lack chlorophyl under comparable light exposures. 4. Basal areas—Commonly white and blending distally to a light yellow green (2.5 GY 8/4) (5 GY 8/4) and/or moderate yellow green (near 2.5 GY 7/6) (2.5 GY 7/4) (near 5 GY 7/6) (5 GY 7/4) at the proximal end of the chlorophyllous center area.

Inflorescence:

*I. Form.*—A. General—Small sessile clusters that appear both in the terminal and in the axil area of the upper leaves.
*II. Flowers.*—A. General—Sessile, actinomorphic, and bisexual with a calyx tube having three connate sepals, a corolla having three petals that seldom open, epipetalous stamens that are usually six in number, anthers that are versatile and linear, filaments that are relatively short and cylindrical, a compound pistil having three carpels, stigma limbs that are three in number, and an inferior ovary containing relatively few ovules. B. Texture—Glabrous and fleshy. C. Shape—Elongated, terete in area of ovary, and expanding distally thereof to an intermediate area that is generally triangular in cross section and then tapering distally of the intermediate area to an acute tip. D. Size—1. Length—Usually less than 18 mm. at full bloom. 2. Maximum transverse dimension (intermediate area) Usually less than 6 mm. E. Color—Commonly white with distal striations which are commonly pale yellow green (5 GY 9/2), light yellow green (near 5 GY 9/4) (5 GY 8/6), and/or moderate yellow green (5 GY 7/6) and with an apex area which is commonly light pink-moderate pink (near 5 R 8/4), moderate pink (5 R 7/6), strong pink (2.5 7/8) (5 R 7/8), and/or deep pink (2.5 R 6/8).

The following is a general description of a specimen of the new plant variety that was grown from the propagation of a vegetative offshoot in a nursery at Winter Garden, Fla., the description being taken at anthesis and during the month of August.

A. Age of plant—Six to ten weeks growth on parent plant and an additional seven months of growth from time of initial propagation.
B. Height of plant (soil to a pex of terminal bloom cluster)—67 mm.
C. Diameter of plant (measured between most wide spread leaf tips at level indicated)—
  *1. Base.*—240 mm.
  *2. Midway between base and apex.*— 190 mm.
  *3. Apex.*—60 mm.
D. Stem—
  *1. Length.*—59 mm.
  *2. Diameter.*—11 mm. at base and 6 mm. at apex.
E. Leaves—
  *1. Number of leaves.*—32.
  *2. Length.*—Ranges from 87 mm. to 147 mm. below apex, and averaging 117 mm.
  *3. Width.*—From 19 mm. to 27 mm. at the widest area distally of the stem sheathing base area and averaging 24 mm.
  *4. Thickness.*—From 1.75 to 3.0 mm. and averaging 2.75 along the axis, and from 0.3 mm. to 0.9 mm. and averaging 0.5 at margin.
  *5. Color.*—a. Albino marginal area—Moderate red (2.5 R 5/10) (5 R 5/10), deep pink (2.5 R 6/10) (2.5 R 6/8) (5 R 6/10) (5 R 6/8), strong pink (2.5 F 7/8), moderate pink (5 R 7/6) (5 R 7/4), strong yellowish pink (5 R 7/8), and moderate yellowish pink (7.5 R 7/4). b. Central area—Dark greyish red (2.5 R 3/2) (5 R 3/2), greyish reddish brown (7.5 R 3/2) (10 R 3/2) in high density chlorophyllous areas. Light greyish reddish brown (5 R 6/2), light greyish brown (5 YR 6/2) (7.5 YR 6/2), light olive brown (2.5 YR 6/2), light brown (5 YR 5/4) (7.5 YR 5/4), and moderate yellowish pink (2.5 YR 7/4) (5 YR 7/4) in chlorophyl containing striations exhibiting albino characteristics. Moderate red (2.5 R 5/10), deep pink (2.5 R 6/10) (5 R 6/10), strong pink (2.5 R 7/8), moderate pink (5 R 7/6) (5 R 7/4), strong yellowish pink (5 R 7/8), and moderate yellowish pink (7.5 R 7/4) in non-chlorophyl containing striations.

F. Inflorescence—

1. *Number of flowers.*—a. Terminal cluster—35. b. Axillary clusters—(1) Number of clusters—5. (2) Flowers per cluster (average)—2.6.

G. Flowers (mature)—

1. *Length.*—From 12 mm. to 16.5 mm. and averaging 14.4 mm.
2. *Maximum transverse dimension (intermediate area).*—Varies from 3.0 to 4.5 mm.
3. *Color.*—White, pale yellow green (5 GY 9/2), light yellow green (5 GY 9/4) (5 GY 8/6), moderate pink (5 R 7/8), strong pink (2.5 R 7/8) (5 R 7/8).

I claim:

1. The new and distinct plant variety of the Bromeliaceae family as illustrated and described and which is principally distinguished by a growth habit that combines the following characteristics:

1. Elongated leaves which have prominent albino marginal areas that in color are dominated by red, pink and/or yellowish pink hues when subjected to prolonged light exposure and which have an intervening prominent chlorophyllous center area that generally extends along and laterally of the leaf axis and has striations which in varying degrees exhibit albino characteristics, and
2. An inflorescence which has fewer and lighter colored flowers with fewer ovules than specimens of the *Cryptanthus bivittatus minor* variety.

References Cited

Exotica 3, Graf, Roehrs. Co., Rutherford, N.J., 1963, pp. 5, 37, 397, 399 401 423–5 1587–8 of interest, AU 337.

R. BAGWILL, Primary Examiner

PO-1050
(5/69)

UNITED STATES PATENT OFFICE
CERTIFICATE OF CORRECTION

Patent No. PP. 3,689 Dated March 11, 1975

Inventor(s) Barnell L. Cobia

It is certified that error appears in the above-identified patent and that said Letters Patent are hereby corrected as shown below:

Column 3, Line 18 before "A." -- Leaves: -- should appear;
Column 4, Line 72 (2.5 F 7/8) should read -- (2.5 R 7/8) --.

Signed and Sealed this

Twenty-seventh Day of July 1976

[SEAL]

*Attest:*

RUTH C. MASON
*Attesting Officer*

C. MARSHALL DANN
*Commissioner of Patents and Trademarks*